United States Patent [19]

Sizto et al.

[11] Patent Number: 5,620,657

[45] Date of Patent: Apr. 15, 1997

[54] DEVICE AND METHOD FOR COMPLETING A FLUIDIC CIRCUIT

[75] Inventors: N. Chung Sizto; Nurith Kurn, both of Palo Alto; Rajesh D. Patel, Fremont; Martin Becker, Palo Alto; Edwin F. Ullman, Atherton, all of Calif.

[73] Assignee: Behringwerke AG, Marburg, Germany

[21] Appl. No.: 453,859

[22] Filed: May 30, 1995

Related U.S. Application Data

[62] Division of Ser. No. 821,338, Jan. 13, 1992, which is a continuation of Ser. No. 441,676, Nov. 27, 1989, abandoned.

[51] Int. Cl.$^6$ .................... G01N 33/558; G01N 21/00
[52] U.S. Cl. ................... 422/56; 422/58; 422/61; 435/7.1; 435/970; 435/975; 436/514
[58] Field of Search .......... 422/56–61; 435/7.1, 435/970, 975; 436/514, 808, 180

[56] References Cited

U.S. PATENT DOCUMENTS

| | | | |
|---|---|---|---|
| 3,482,943 | 12/1969 | Csizmas et al. . | |
| 3,888,629 | 6/1975 | Bagshawe . | |
| 3,918,920 | 11/1975 | Barber | 422/104 |
| 4,094,647 | 6/1978 | Deutsch et al. . | |
| 4,246,339 | 1/1981 | Cole et al. . | |
| 4,426,451 | 1/1984 | Columbus | 422/58 |
| 4,435,504 | 3/1984 | Zuk et al. . | |
| 4,477,575 | 10/1984 | Vogel et al. | 422/56 |
| 4,549,655 | 10/1985 | Forsythe, Jr. et al. | 422/58 |
| 4,700,714 | 10/1987 | Fuisz . | |
| 4,740,468 | 4/1988 | Weng et al. . | |
| 4,803,170 | 2/1989 | Stanton et al. . | |
| 4,826,759 | 5/1989 | Guire et al. | 435/805 |
| 4,839,297 | 6/1989 | Freitag et al. | 435/805 |
| 4,849,340 | 7/1989 | Oberhardt | 422/58 |
| 4,861,711 | 8/1989 | Friesen et al. | 422/56 |
| 4,883,764 | 11/1989 | Kloepfer | 422/58 |
| 4,891,313 | 1/1990 | Berger et al. | 430/512 |
| 4,902,629 | 2/1990 | Meserol et al. | 436/165 |
| 4,959,324 | 9/1990 | Ramel et al. | 422/58 |
| 4,987,085 | 1/1991 | Allen et al. | 422/58 |
| 5,079,142 | 1/1992 | Coleman et al. | 422/56 |
| 5,079,174 | 1/1992 | Buck et al. | 422/56 |
| 5,082,626 | 1/1992 | Grage et al. | 422/58 |
| 5,104,811 | 4/1992 | Berger et al. | 422/58 |
| 5,114,673 | 5/1992 | Berger et al. | 422/56 |
| 5,135,873 | 8/1992 | Patel et al. | 422/55 |

FOREIGN PATENT DOCUMENTS

| | | |
|---|---|---|
| 1185882 | 4/1985 | Canada . |
| 146691 | 7/1985 | European Pat. Off. . |

*Primary Examiner*—Jill Warden
*Assistant Examiner*—Jan M. Ludlow
*Attorney, Agent, or Firm*—Theodore J. Leitereg

[57] ABSTRACT

Disclosed are assay apparatus, devices and methods that permit longitudinal capillary flow of liquid between two pieces of bibulous material which, prior to actuation, are in a non-capillary flow relationship to each other. In particular, the devices utilize a distortable member which when distorted, actuates the device by creating a capillary flow relationship between the two pieces of bibulous material. In an alternative embodiment the apparatus, devices, and methods include at least one additional piece of bibulous material.

9 Claims, 6 Drawing Sheets

DEVICE AND METHOD FOR COMPLETING A FLUIDIC CIRCUIT

This is a Division of application Ser. No. 07/821,338 filed Jan. 13, 1992, which is a File Wrapper Continuation of application Ser. No. 07/441,676, filed Nov. 27, 1989, now abandoned, the disclosures of which are incorporated herein by reference.

BACKGROUND OF THE INVENTION

1. Field of the Invention

The present invention is directed to assay apparatus, devices and methods that permit longitudinal capillary flow of liquid between two pieces of bibulous material and that, prior to actuation, are in a non-capillary flow relationship to each other. In particular, the device utilizes a distortable member which when distorted, actuates the device and a capillary flow relationship is initiated between the two pieces of bibulous material. The methods, apparatus, and devices of the present invention have utility in conducting assays which use capillarity to transport solutions and/or samples including assays such as enzyme immunoassays, fluorescent immunoassays, radioimmunoassays, etc.

2. Related Art

Assay devices have been described in which liquid is transported by capillarity through or transversely along a bibulous support thereby transporting reagents and samples to sites on the support and/or washing the support. Such devices have been described by Deutsch, U.S. Pat. No. 4,094,647; Zuk et al, U.S. Pat. No. 4,435,504; Weng et al, U.S. Pat. No. 4,740,468; Friesen et al, German Offenlengungschrift 3,445,816 etc.

In many of these methods, reagents can be added at more than one position on the bibulous support. In such situations, it is often desirable to cause the added reagent to migrate in only one direction along the bibulous support, to delay flow in a given direction, or to create a direction of flow that was impeded prior to the addition of the reagent. For example, it is often desirable for a solution moving along a bibulous support to automatically stop moving after a certain volume has been taken up so as to avoid the necessity to monitor the flow of solution. Subsequent to taking up a certain volume, a second solution is allowed to flow along the support. In the past, the first flow could be stopped by limiting the length of the first bibulous support and the second flow initiated by contacting one end of the first bibulous support with a solution and the other end with a second bibulous support which is dry.

Likewise, in liquid containing assay devices, a sample is added to one of the ports and liquid within the device washes the sample away from a detection zone. See, for instance, Khanna et al, U.S. patent application Ser. No. 35,562 filed Apr.7, 1987 entitled "Immunoassay Devices". To maximize the washing efficiency, it is desirable that upon contacting the support with the sample, the sample flows in only the direction away from the source of the wash liquid.

In both of the above cases, it is desirable to create a capillary flow relationship between pieces of bibulous material which heretofore have been in a non-capillary flow relationship. Moreover, it would be particularly desirable to create such a capillary flow relationship automatically without mechanical means external to the device while requiring minimal operator involvement to operate.

U.S. Pat. No. 3,482,943 discloses expandable sponges useful in transporting solution to a set position on a gel suitable for conducting immunodiffusion tests. In this reference, the solution transported by the sponge is allowed to diffuse into the gel which, in order to conduct the immunodiffusion, is by necessity a wet gel. Accordingly, no capillary flow relationship between the expandable sponge and the gel is established by this device.

U.S. Pat. No. 4,246,339 discloses a device having an upper portion and a lower portion. The upper portion has a plurality of wells wherein the bottom of each well is fitted with a membrane layer capable of transporting liquid. The bottom portion of the device contains absorbent material. Between the top and bottom portions is a compressible spacer. This device allows a liquid sample to be added to the wells which may optionally be impregnated with an antibody. After a set incubation period, pressure is placed on the top portion which because of the compressible spacer, allows the bottom of each of the wells to contact the absorbent material whereupon the liquid in the wells is transferred to the absorbent material. After liquid transfer, the pressure is removed and contact between the bottom of the wells and the absorbent material is broken. Thereupon, additional liquid may be added to the wells. In this device, care must be taken to insure that the bottom of all of the wells come into contact with the absorbent material for a sufficient period of time to remove the liquid. In particular, if one or more of the wells does not contact the absorbent material, then the liquid in that well will not be removed. Moreover, if one or more of the wells does not contact the absorbent material for a sufficient period of time, then not all of the liquid in that well will be removed. In any case, a high level of operator care is required to ensure the proper operation of this device.

U.S. Ser. No. 35,562 filed Apr. 7, 1987 entitled "Immunoassay Devices" discloses a device for conducting an assay method. The device comprises a housing having in one portion thereof a breakable capsule and in another portion a piece of bibulous material attached to an absorbent pad.

European Patent Application Publication No. 0 146 691 discloses an air bleed passage in a liquid sampling needle which is formed between a housing and a sleeve and into which is added a solid compacted material which swells on contact with liquid. As the liquid sample is drawn into the needle, air can escape via the air bleed until the air bleed is contacted with liquid whereupon it expands and forms a liquid impermeable membrane.

U.S. Pat. No. 4,700,741 discloses a urine collecting device which contains an expandable sponge in a compartment which permits the collection of a predetermined quantity of urine by limiting expansion of the sponge within the compartment.

Canadian Patent No. 1,185,882 discloses porous, hydrophilic, non-gel-forming swellable polymers or self-drawing fluid reservoirs with a very high and uniform absorption and release of fluid in a chromatographic quick-test device.

U.S. Pat. No. 4,826,759 describes apparatuses and methods, which can be used in the field (i.e., outside the laboratory environment) to determine qualitatively and at least semiquantitatively the presence or absence of minute quantities of ligand. The apparatus can be in the form of a strip comprising a support means provided with a groove intermediate its ends forming a crease line upon which the strip can be folded upon itself with bibulous elements and spaced from the crease line and arranged so that when the strip is folded upon itself the bibulous elements become aligned with each other and come into liquid contact.

U.S. Pat. No. 4,803,170 discusses an immunoassay device including one or more reaction chambers, each adapted to receive and retain a volume of test fluid communication with non-overlapping first, second, and third reagent-bearing surfaces. To the first surface is reversibly bound an analyte conjugate: Analyte component conjugated to one or more components, termed ligand/marker, that serve ligand and marker functions as described herein. Analyte binding partner is immobilized on the second surface, and ligand/marker binding partner is immobilized on the third surface. The reaction chamber is preferably configured to receive and direct the test fluid sequentially past the first, second, and third reagent surfaces. In use, analyte conjugate solubilized from the first surface competes with any analyte in the test fluid for analyte binding partner sites on the second surface. Excess analyte conjugate becomes sequestered on the third surface, where the marker activity is read to indicate analyte presence and concentration in the test fluid. A test kit includes the immunoassay device in combination with comparative test results.

U.S. Pat. No. 3,888,629 describes a reaction cell for the performance of radioimmunoassay determinations and like saturation analysis reactions that has supported within it a matrix pad of absorbent material capable of retaining the necessary reagents for the reaction and serving as a site in which the reaction totally occurs. A separable lower chamber is fitted to the lower end of the cell and contains absorbent material to abut the matrix pad and promote filtration through the pad after the reaction has taken place. An upper reservoir chamber fits to the upper end of the cell to contain liquid for passing through the matrix pad. The matrix pad will commonly contain prior to the reaction a predetermined amount of an antigen or antibody in freeze-dried condition and possibly radioactivity labelled.

Accordingly, there is a need for a device for creating a capillary flow relationship between pieces of bibulous material which prior to actuation, are in a non-capillary flow relationship to each other. Preferably, such a device should require minimal operator involvement to operate.

SUMMARY OF THE INVENTION

The present invention is directed to assay apparatus, devices and methods that permit longitudinal capillary flow of liquid through two pieces of bibulous material, which prior to actuation are in a non-capillary flow relationship to each other. In particular, in one of its device aspects, the present invention is directed to a device for use in an assay that permits capillary flow of a liquid through two pieces of bibulous material which prior to actuation are in a non-capillary flow relationship to each other which comprises (a) two pieces of bibulous material in a non-capillary flow relationship to each other and (b) a distortable member, which when distorted actuates the device by creating a longitudinal capillary flow relationship between the two pieces of bibulous material. The distortable member may have affixed thereto a third piece of bibulous material in a non-capillary flow relationship with the two pieces of bibulous material in (a) above or the distortable member may comprise a portion of one of the two pieces of bibulous material.

In one of its method aspects, the present invention is directed toward a method for carrying out an assay that comprises using a longitudinal capillary flow relationship between two pieces of bibulous material, which prior to creating the relationship are in a non-capillary flow relationship to each other. The method comprises the step of contacting two pieces of bibulous material, each in a non-capillary flow relationship to the other, with a distortable member so as to achieve a longitudinal capillary flow relationship between the pieces. The distortable member may comprise a portion of one of the two pieces of bibulous material. Alternatively, a third piece of bibulous material can be affixed to the distortable member and contacting of the pieces can be obtained by distorting the distortable member.

In another embodiment the distortable member may include a portion of one of the two pieces of bibulous material. The two pieces of bibulous material may be affixed to a support, where a portion of one of the two pieces is not supported by the support and is therefore distortable. The support can be adapted for insertion into a housing. One or more flexible members, may be attached to the housing. In this embodiment the support is inserted into the housing and one of the flexible members forces the distortable portion, usually an adjacent end of one of the two pieces of bibulous material, into contact with an adjacent end of the other.

In another of its method aspects, the present invention is directed toward a method for carrying out an assay by creating a longitudinal capillary flow relationship between two pieces of bibulous material which prior to actuation are in a non-capillary flow relationship to each other which comprises (a) providing a device which comprises (i) two pieces of bibulous material in a non-capillary flow relationship to each other, and (ii) a distortable member, and (b) distorting the distortable member which thereby results in contact of the pieces of bibulous material so as to achieve a longitudinal capillary flow relationship between the pieces of bibulous material.

The invention further includes kits and apparatus.

DETAILED DESCRIPTION OF THE INVENTION

Assay devices, apparatus and methods are provided which permit the formation of a capillary flow relationship between two pieces of bibulous material. In particular, the devices of the present invention are useful for assays in which a longitudinal capillary flow relationship is created between two pieces of bibulous material which theretofore were in a non-capillary flow relationship to each other.

The devices of the present invention are adaptable to a wide variety of analytical uses which require a capillary flow relationship between pieces of bibulous materials which prior to actuation, were in a non-capillary flow relationship. The devices of the present invention are particularly suited for use in conjunction with chromatographic methods, particularly those providing assays for biologically significant analytes. The devices are particularly suited for clinical assay methods including immunoassays such as radioimmunoassays, enzyme immunoassays, fluorescent immunoassays, etc.

Before proceeding further with the description of the specific embodiments of the present invention, a number of terms will be defined.

Bibulous material—a porous material having pores of at least 0.1 μm, preferably at least 1.0 μm, which is susceptible to traversal by a liquid medium, for example, an aqueous medium, in response to capillary force. Such materials are generally hydrophilic or hydrophobic depending on whether the liquid medium is polar or non-polar, respectively, or are capable of being rendered hydrophilic or hydrophobic and include inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as polystyrene, polyethylene, nitrocellulose, cellulose acetate, poly(vinyl chloride), polyacrylamide, cross-linked dextran, agarose, polyacrylate, etc.; either used by themselves or in conjunction with other materials; ceramic materials; and the like. The bibulous material can be attached to a support. On the other hand, the bibulous material may provide its own support. The bibulous material may be polyfunctional or be capable of being polyfunctionalized. The bibulous material employed in the present invention is not susceptible to expansion when exposed to liquid. That is to say when wetted, the bibulous material will not expand by more than about 10%; although preferably by no more than about 5%.

The pieces of bibulous material can be a single structure such as a sheet cut into strips or it can be several strips or particulate material bound to a support or solid surface such as found, for example, in thin-layer chromatography and may have an absorbent pad either as an integral part or in liquid contact. The piece of bibulous material can be comprised of several segments, one or more being an absorbent pad, bound to a support. The piece of bibulous material can also be a sheet having lanes thereon or capable of spotting to induce lane formation, wherein a separate assay can be conducted in each lane. The absorbent pad may be any hydrophilic bibulous material such as paper, sponge, felt, porous polymers and the like. The piece of bibulous material can have a rectangular, circular, oval, triagonal or other shape provided that there is at least one longitudinal direction of traversal of a liquid test solution by capillary migration that is at least 10 times the thickness of the piece and is preferably at least 20 or more times the thickness of the piece. Such a situation gives rise to a longitudinal capillary flow relationship as the term is used herein. In the following discussion, strips of bibulous material will be described by way of illustration and not limitation.

The support for the bibulous material, where a support is desired or necessary, will normally be insoluble in the liquid medium, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or, in the case where the bibulous material is used in an assay, non-specifically bind assay components, or interfere with the signal produced by the assay. Illustrative polymers include polyethylene, polypropylene, poly(4-methylbutane), polystyrene, polymethacrylate, poly(ethylene terephthalate), nylon, poly(vinyl butyrate), glass, ceramics, metals, and the like.

The pieces of bibulous material used in the present invention need not be comprised of the same bibulous substance. For example, in an embodiment utilizing three pieces of bibulous material, two of the pieces of bibulous material can be comprised of silica whereas the third piece of bibulous material can be comprised of alumina. However, in a preferred embodiment, all of the pieces of bibulous material are comprised of the same bibulous substance.

Non-capillary flow relationship—two pieces of bibulous material are in a non-capillary flow relationship when liquid is unable to move by capillarity, i.e., capillary migration, from the first piece to the second piece of bibulous material. One manner of creating a non-capillary flow relationship between two pieces of bibulous material is to prevent any contact between the pieces. On the other hand, the two pieces may be in contact with each other but capillary flow between the pieces may be prevent by a physical or chemical barrier. In this case, these two pieces are in a non-capillary flow relationship to each other.

Longitudinal capillary flow relationship—two pieces of bibulous material are in a longitudinal capillary flow relationship when liquid is able to move by capillarity, i.e., capillary migration, from one piece to the other piece of bibulous material and thereby provide for capillary flow along a long dimension of at least one of the pieces wherein the long dimension is at least 10 times the length of the shortest dimension of the piece measured perpendicular to the direction of flow. As shown by the present invention, one manner of creating a longitudinal capillary flow relationship between two pieces of bibulous material is to utilize a third piece of bibulous material which contacts both the first and second piece of bibulous material so as to complete a fluidic circuit among all three pieces of bibulous material. Another manner of creating a longitudinal capillary flow relationship between two pieces of bibulous material is to employ a distortable member to force adjacent ends of the pieces into contact with each other.

Distortable member—a member which under applied pressure is capable of being bent, constricted or compressed or otherwise moved to cause two pieces of bibulous material to come into intimate contact and thereby initiate a longitudinal capillary flow relationship between the two pieces of bibulous material. At least a portion of the distortable member lies substantially opposite the adjacent ends of the two pieces of bibulous material, i.e., the ends that will be involved in forming the capillary flow relationship between the two pieces of bibulous material. The two pieces of bibulous material are generally affixed to the same surface, but need not be. The distortable member can have a third piece of bibulous material affixed thereto. Where the device does not include a third piece of bibulous material, the distortable member can comprise a portion of one of the two pieces of bibulous material.

In one embodiment, the distortable member is part of a device having two arms, wherein the arms preferably lie substantially parallel to each other and are connected to each other through a central shoulder. In this embodiment, at least one of the arms is capable of being constricted or compressed or bent toward the other arm when a force is applied to that arm with a directional component running substantially perpendicular to and toward the other arm. Also, in this embodiment, the distortable member is that arm which has a piece of bibulous material which contacts the two other pieces of bibulous material regardless of which arm actually moves. Thus, the distortable member may have its position fixed by attachment to a wall or support and the other arm may move in relationship to the distortable member or the other arm may be attached to a wall and the distortable member may move. However, in either case, upon distortion, the piece of bibulous material on the distortable member will contact the two other pieces of bibulous material on the other arm thereby initiating a capillary flow relationship among all three pieces of bibulous material.

In this embodiment, the distortable member is attached to a shoulder which is comprised of a flexible material such as a semi-rigid plastic or a pliable metal which allows at least one of the arms of the distortable member to be susceptible to compression (in the direction of the other arm) by applied pressure. Generally, the flexible material should be sufficiently pliable so as to result in compression of at least one of the arms by the pressure resulting from squeezing, etc. In general, two pieces of bibulous material are positioned on one arm (in a non-capillary flow relationship to each other) and the third piece of bibulous material is positioned on the distortable member (other arm) in such a manner that upon distortion, the third piece of bibulous material contacts both the two other pieces of bibulous material so as to result in the formation of a capillary flow relationship among the three pieces.

In another embodiment, the distortable member having a third piece of bibulous material affixed thereto is part of a device wherein the two pieces of bibulous material are attached to a surface of a support having a fixed position. In this embodiment, the distortable member is capable of constricting or compressing or bending in the direction of this support. Such constriction is generally the result of movement by applying a force to the distortable member around a shoulder comprised of flexible material or a hinge.

In another embodiment the distortable member is a portion of one of the two pieces of bibulous material. The two pieces of bibulous material are fixedly attached to a support where a portion of one of the pieces extends beyond the support. The support is adapted for insertion into a housing having one or more flexible members. In a method in accordance with the invention the support is inserted into the housing. The distortable portion of one of the pieces of bibulous material bends, when contacted by a flexible member, and is forced to contact an adjacent end of the other piece of bibulous material. As a result a longitudinal capillary flow relationship is initiated between the two pieces of bibulous material, thus achieving actuation of the device.

Analyte—the compound or composition to be measured that is capable of binding specifically to an antibody, usually an antigen or drug.

The precise nature of the antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes are characterized by having single binding sites (monovalent) or multiple binding sites (polyvalent).

The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes, and the like.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like.

For receptor analytes, the molecular weights will generally range from 10,000 to $2\times10^8$, more usually from 10,000 to $10^6$. For immunoglobulins IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member")—one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin hormones-hormone receptors, nucleic acid duplexes, IgG-protein A, DNA-DNA, DNA-RNA, and the like are not immunological pairs but are included in the definition.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq. and the like.

Labeled sbp member—a label, generally capable of electrochemical detection or absorption or emission of electromagnetic radiation, a catalyst, frequently an enzyme, bound to a first sbp member. The labeled sbp member is a member of the signal producing system and the first sbp member is chosen to bind to the second sbp member in accordance with a particular protocol in an assay.

Antibody—an immunoglobin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for the analyte—an antibody specific for an analyte.

First sbp member—a modified analyte or analyte analog or surrogate which can compete with the analogous analyte in binding to a second sbp member, usually a receptor or antibody, the modification providing means to join the analyte analog to a label to provide a labeled sbp member. The analyte analog will usually differ from the analyte by more than replacement of a hydrogen with a bond which links the analyte analog to a hub or label, but need not. The term analyte surrogate refers to a compound having the capability of binding the antibody for the analyte. Thus, the analyte surrogate may bind to the antibody for the analyte in a manner similar to the analyte. On the other hand, the surrogate could be, for example, an antibody directed against the idiotype of an antibody to the analyte.

The first sbp member can also be a conjugate of an analyte, a label, e.g., enzyme, and a third sbp member.

Second sbp member—an sbp member capable of binding to the analyte and the first sbp member. The second sbp member can bind to a determinant site on the analyte and to a determinant site on the first sbp member. A preferred second sbp member is an antibody.

Binding agent—a material non-diffusively bound to the situs capable of binding the first sbp member. The material may bind non-specifically or specifically. When the binding is non-specific, the binding agent will usually be hydrophobic or polyionic. When the binding agent provides for specific binding, it will usually be an sbp member complementary to the labeled sbp member, preferably a receptor for the first sbp member. As a practical matter, the binding agent will usually be the second sbp member, but it may be either member of a large variety of specific binding pairs, provided only that the complementary member is bound to the labeled sbp member. When the first sbp member is a conjugate comprising an analyte, a label, and a third sbp member, the binding agent can be a corresponding receptor for the third sbp member.

Label—A label may be any molecule bound to the first member that is required to produce a signal. In the subject invention, the label may be inert and serve solely as a binding site for a member of the signal producing means or it may spontaneously produce a detectable signal or may produce a detectable signal in conjunction with a signal producing means. The label may be isotopic or nonisotopic, preferably nonisotopic. However, an isotopic label can be preferred for achieving high sensitivity when using radioautographic detections with photographic film.

Signal producing means—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the strip.

Signal producing system—The signal producing system may have one or more components, at least one component being the labeled sbp member. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

Ancillary Materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly, non-ionic surfactants, binding enhancers, e.g. polyalkylene glycols, or the like.

Figure 1:
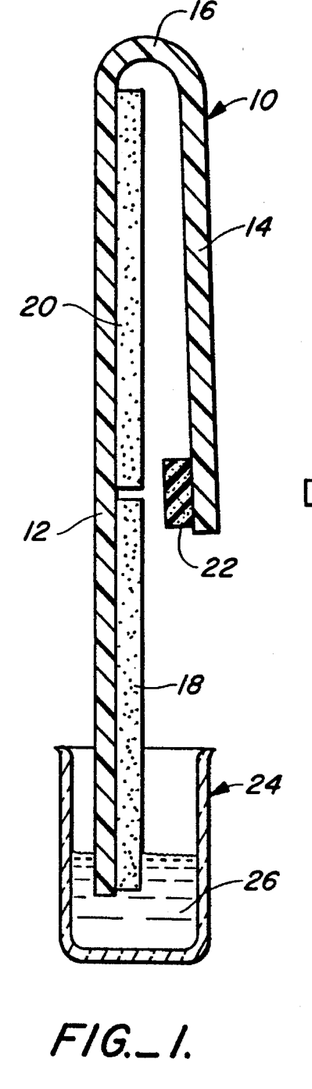
FIG. 1 is a cross-sectional view of one embodiment of this invention in its unactuated state.

Referring now to the drawings, FIG. 1 is a cross-sectional view of one embodiment of this invention. In FIG. 1, device 10 contains two arms 12 and 14 attached through shoulder 16. Arm 12 contains a first and second piece of bibulous material 18 and 20, respectively; whereas arm 14 contains a piece of bibulous material 22. Arm 14, which contains only one piece of bibulous material, is also referred to as the distortable member. Because none of the pieces of bibulous material are in a capillary flow relationship with any other piece of bibulous material, device 10 is in its unactuated state. The bottom portion of piece of bibulous material 18 of device 10 is designed to be inserted into a container 24 having a liquid solution 26 which can traverse by capillarity at least that portion of piece of bibulous material between liquid solution 26 and the portion of bibulous material 18 capable of contact with bibulous material 22.

Figure 2A:
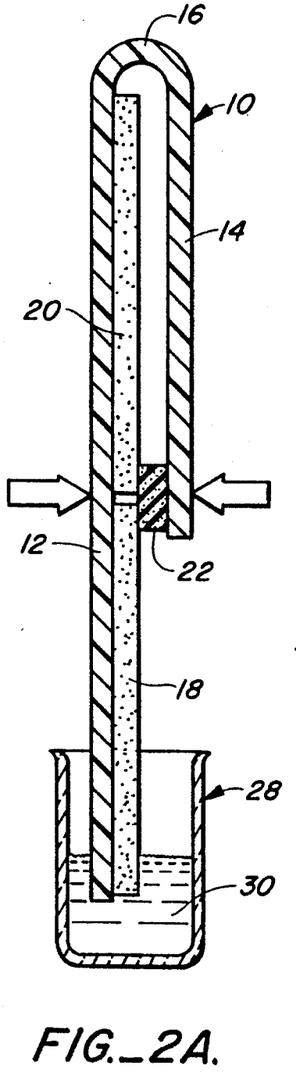
FIG. 2A illustrates the device depicted in FIG. 1 in an actuated state.

FIG. 2A illustrates one method of actuating the device of FIG. 1. In particular, the bottom portion of piece of bibulous material 18 of device 10 is generally inserted into a second container 28 with a liquid solution 30 and is actuated by applying inward pressure on the outer surfaces of arms 12 and 14. Sufficient force is applied to ensure that piece of bibulous material 22 is brought into contact with both the top portion of piece of bibulous material 18 and the bottom portion of piece of bibulous material 20. In general, sufficient force can be applied either mechanically or manually, preferably mechanically, by squeezing together arms 12 and 14. Mechanical means of applying sufficient force include squeezing arms 12 and 14 by insertion into a slot in a device designed to provide a uniform pressure at the bibulous material contact surfaces sufficient to cause liquid flow without compressing the bibulous material to such an extent that flow is restricted. Shoulder 16 of device 10 is comprised of a flexible material which allows the arms to be susceptible to compression by applied pressure. The flexible material should be sufficiently pliable so as to result in compression when pressure is applied. Suitable flexible materials include semi-rigid plastics and pliable metal.

Figure 2B:
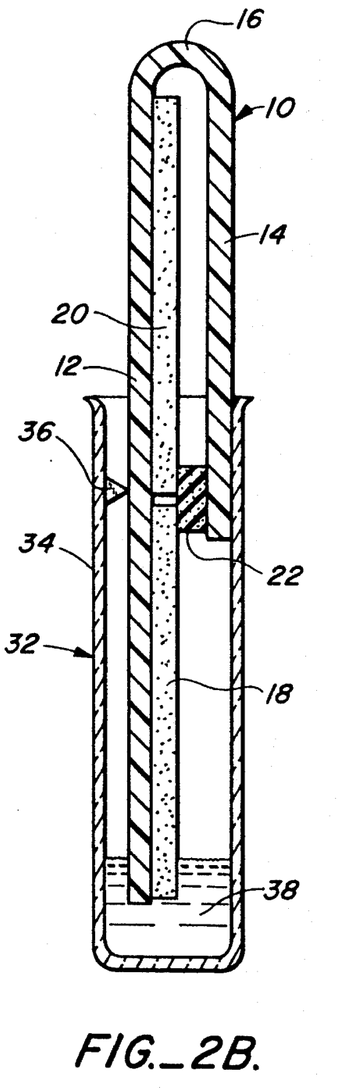
FIG. 2B illustrates the device depicted in FIG. 1 in an actuated stated.

FIG. 2B illustrates another method of actuating the device of FIG. 1. In particular, device 10 is actuated by applying inward pressure on the outer surfaces of arms 12 and 14. Sufficient pressure is applied to ensure that piece of bibulous material 22 is brought into contact with both the top portion of piece of bibulous material 18 and the bottom portion of piece of bibulous material 20. In FIG. 2B, device 10 is actuated by inserting this device into container 32 having wall 34, protrusion 36 and liquid solution 38. By virtue of limited space in container 32, arms 12 and 14 are constricted or compressed toward each other which results in piece of bibulous material 22 contacting pieces of bibulous material 18 and 20. When such contact is made, all three pieces of bibulous material are in a capillary flow relationship to each other.

Arms 12 and 14, container 32 as well as protrusion 36 are generally comprised of any non-corrodable materials which do not readily degrade or disintegrate upon exposure to the solutions employed in the assay or test. Additionally, such materials should not interfere with the assay or test being conducted. In general, metals, metal alloys, glass and rigid and semi-rigid plastics can be used. Preferably, glass or a rigid plastic is employed. As used herein, the term "non-corrodable" means that the material is not subject to undo decomposition or disintegration when routinely used in the devices of the present invention.

Device 10 is generally operated in the following manner; the bottom portion of bibulous material 18 of device 10 is inserted into a first solution 26. This solution is allowed to traverse all or part of bibulous material 18 by capillarity. Because piece of bibulous material 18 is not in a capillary flow relationship with either piece of bibulous material 20 or 22, once solution 26 reaches the top end of piece of bibulous material 18, capillary flow ceases. The wetted bibulous material may then be incubated in contact with solution 26 and/or device 10 may be withdrawn from solution 26 and the bottom portion of piece of bibulous material 18 is inserted into solution 30 or 38 which is preferably a solution different from solution 26. In the situation set forth in FIG. 2A, device 10 is then actuated which results in piece of bibulous material 22 contacting both piece of bibulous material 18 and piece of bibulous material 20 thereby creating a longitudinal capillary flow relationship among all three pieces of bibulous material. Because pieces of bibulous material 22 and 20 are dry, capillary flow will be reinitiated until either the solution is exhausted or all of the pieces of bibulous material are completely wetted. Bibulous materials 18 and/ or 20 can have appropriate reagents bound at predetermined sites thereon. See, for instance, Zuk et al, U.S. Pat. No. 4,435,504; Weng et al, U.S. Pat. No. 4,740,468; and Tom et al, U.S. Pat. No. 4,366,241, the disclosure of each of which is incorporated herein in their entirety by reference.

In the situation set forth in FIG. 2B, device 10 is actuated by insertion into container 32 which results in piece of bibulous material 22 contacting both piece of bibulous material 18 and piece of bibulous material 20 thereby creating a longitudinal capillary flow relationship among all three pieces of bibulous material. Because pieces of bibulous material 22 and 20 are dry, capillary flow will be reinitiated until either the solution is exhausted or all of the pieces of bibulous material are completely wetted.

In another embodiment not shown in either FIG. 2A or 2B, an absorbent pad may be in liquid receiving contact, i.e., in capillary flow relationship, with the upper terminus of piece of bibulous material 20. This embodiment permits greater quantities of liquid to be moved by capillarity along pieces of bibulous material 18, 22 and 20.

Figure 3:
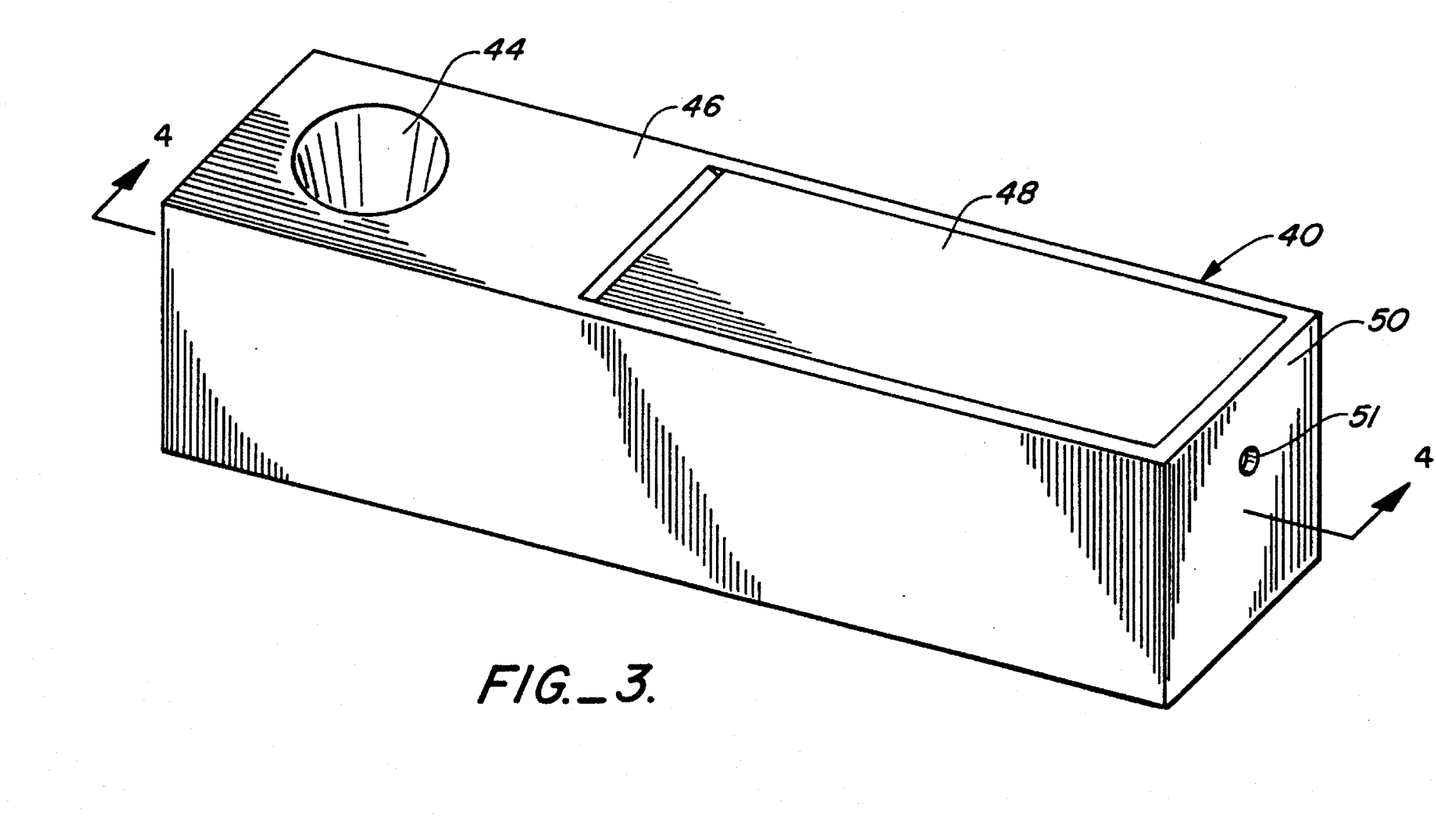
FIG. 3 is a perspective view of another embodiment of this invention.

FIG. 3 is a perspective view of another embodiment of a device of the present invention. In FIG. 3, device 40 is encased by housing 42 which in turn has portal 44 which allows a liquid sample to be placed on piece of bibulous material 54 (shown in FIGS. 4A and 4B). Device 40 has a top wall 46 which has a distortable member 48 and hinge 50. Hinge 50 allows distortable member 48 to move under applied pressure downward in relationship to top wall 46.

Figure 4A:
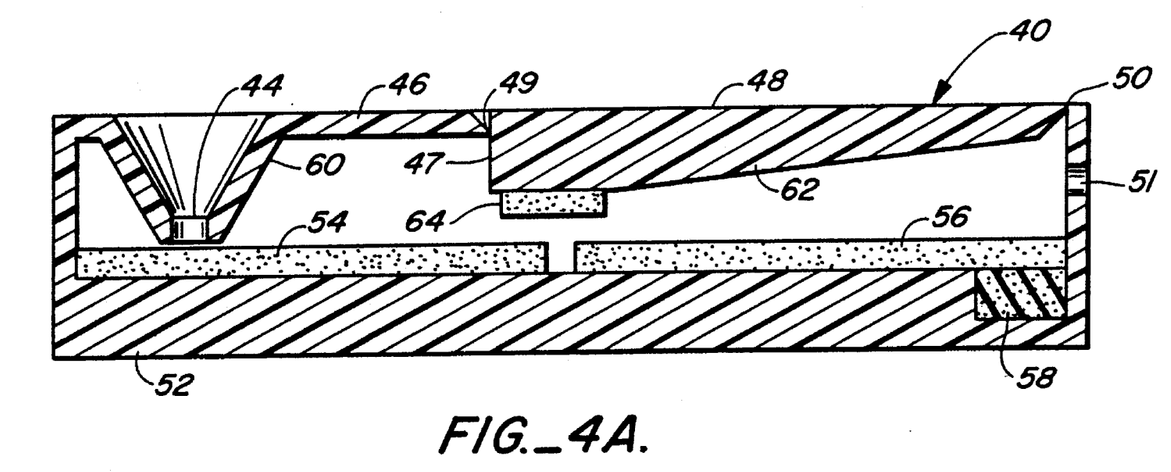
FIG. 4A is a cross-sectional view of the device of FIG. 3 taken along lines 4—4 of FIG. 3 and illustrates this device in an unactuated state.

FIG. 4A illustrates in cross-section the interior of device 40 in its unactuated state. Device 40 contains a bottom surface 52 on the top of which is attached a first piece of bibulous material 54 and a second piece of bibulous material 56. Pieces of bibulous material 54 and 56 do not contact each other and accordingly, are in a non-capillary flow relationship to each other. Second piece of bibulous material 56 is in a capillary flow relationship with an absorbent pad 58. Downward protrusion 60 of top wall 46 form conical portal 44 which is preferably in contact with piece of bibulous material 54 and facilitates the addition of liquid sample (not shown) to piece of bibulous material 54. While portal 44 is conical in nature in FIG. 4A, it need not be. Distortable member 48 has a downward protrusion 62 which terminates in piece of bibulous material 64 which is positioned to overlap both first and second pieces of bibulous material 54 and 56. Distortable member 68 has frangible connection 49 with top wall 46. In its unactuated state, piece of bibulous material 64 does not contact either first or second piece of bibulous material 54 and 56 respectively and therefore all three pieces of bibulous material are in a non-capillary flow relationship to each other.

Figure 4B:
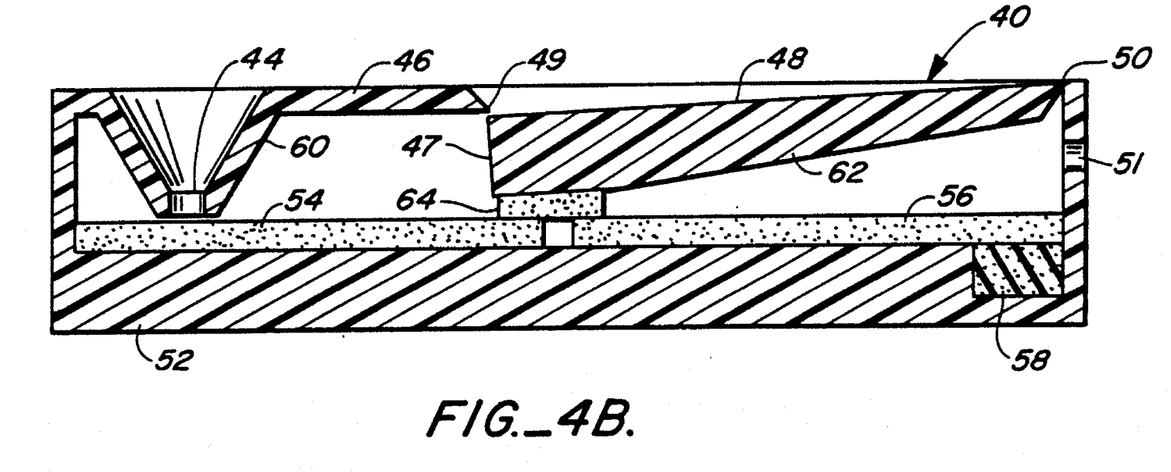
FIG. 4B illustrates the device depicted in FIG. 4A in an actuated state.

FIG. 4B illustrates in perspective the interior of device 40 in its actuated state. As shown in this figure, device 40 is actuated by the downward movement of distortable member 48 wherein frangible connection 49 is broken. The downward movement of 48 results in piece of bibulous material 64 contacting both first and second piece of bibulous material 54 and 56 respectively thereby creating a capillary flow relationship among all three pieces of bibulous material. Distortable member 48 is moved downward through hinge 50 by use of applied downward pressure such as that resulting from a thumb or finger pushing downward on distortable member 48. When wall 47 of distortable member 48 moves past point 49, member 48 is held in position because top wall 46 extends slightly over member 48 at point 49.

In operation, device 40 is utilized by first placing a liquid sample on bibulous material 54 through portal 44. Where protusions 60 forming portal 44 are in contact with piece of bibulous material 54, portal 44 directs the liquid sample to the appropriate position on piece of bibulous material 54. Alternatively, if portal 44 is not in contact with piece 54 but merely is an opening in top wall 46, then the liquid sample can be added to piece of bibulous material 54 by inserting a syringe or pipette through portal 44. Preferably, portal 44 is positioned at or very near the end of bibulous material 54 furthest away from piece of bibulous material 56. The amount of liquid sample should be kept to no greater than the amount that can be absorbed by piece of bibulous material 54. Bibulous materials 54 and/or 56 can have appropriate reagents bound at predetermined sites thereon. See, for instance, Zuk et al, U.S. Pat. No. 4,435,504; Weng et al, U.S. Pat. No. 4,740,468; and Tom et al, U.S. Pat. No. 4,366,241, the disclosure of each of which is incorporated herein in their entirety by reference. After application of liquid sample to piece of bibulous material 54, any additional reagents can be added via portal 44. In this regard, after piece of bibulous material 54 has been completely wetted, device 10 can be actuated by applying pressure on distortable member 48 which results in piece of bibulous material 64 contacting both piece of bibulous material 54 and piece of bibulous material 56. Because pieces of bibulous material 56 and 64 are dry and further because piece of bibulous material 56 is in a longitudinal capillary flow relationship with absorbent pad 58, a capillary flow relationship is initiated among all pieces of bibulous material which will continue until either the solution is exhausted or all of the pieces of bibulous material (including the absorbent pad) are completely wetted. Accordingly, after actuation of device 40, additional liquid reagents, i.e., wash solutions, solutions containing reagents required in the assay or test, etc., can be added to piece of bibulous material 54 via portal 44 and transported along by capillary action.

Alternatively, additional liquid reagents can be added to piece of bibulous material 54 by use of a breakable capsule such at that disclosed in U.S. Ser. No. 35,562 filed Apr. 7, 1987 entitled "Immunoassay Device" and which is incorporated herein in its entirety by reference. Yet another method of adding additional liquid to piece of bibulous material 54 can be accomplished by use of an expandable piece of bibulous material either by itself or in conjunction with a breakable capsule as disclosed in our patent application entitled "Device and Method for Completing a Fluidic Circuit Which Employs a Liquid Expandable Piece of Bibulous Material" which is to be filed concurrently with the instant application and which is incorporated herein in its entirety by reference. In such a case, device 40 would be modified so as to incorporate a liquid expandable piece of bibulous material and optionally, a breakable capsule.

In a preferred embodiment, top wall 46 of device 40 contains a means to view all or a portion of bibulous material 54. One means for viewing bibulous material 54 is by having an appropriate window in top wall 46. Such a window can take the form of a glass or clear plastic encompassing all of top wall 46 or only that portion of top wall 46 which exposes the relevant portion of bibulous material 54. In this regard, many assays which utilize bibulous material have a small detection zone relative to the size of bibulous material employed which upon completion of the assay, indicates the presence or absence of the material being tested for. Accordingly, in those circumstances, it is not necessary to view the entire length of bibulous material 54 but only necessary to view the detection zone. On the other hand, some assays require that the entire bibulous material be viewed in order to quantitatively determine the presence of analyte. The window can also take the form of an opening in top wall 46 which allows viewing of the relevant portion of bibulous material 54.

Figure 5A:
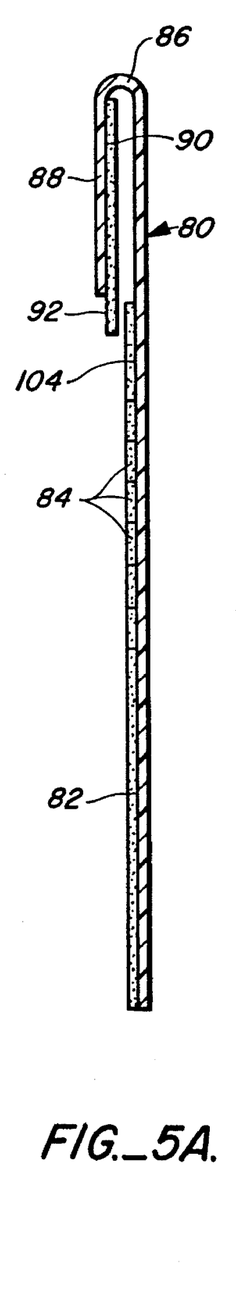
FIG. 5A is a side view of another embodiment of a device in accordance with the present invention.
Figure 5B:
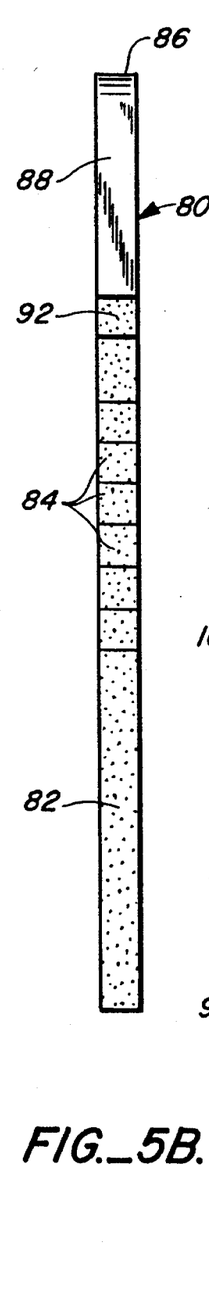
FIG. 5B is a front view of the device shown in FIG. 5A.

Referring now to FIGS. 5A and 5B rigid support 80 has fixedly attached thereto first strip of bibulous material 82 having thereon a series of zones 84 in each of which are bound sbp members. Support 80 turns back on itself at portion 86 to yield portion 88 that has second strip of bibulous material 90 fixedly attached thereto. Second strip 90 faces towards first strip 82 and has distortable portion 92, which extends below portion 88 of support 80 and serves as a distortable member.

Support 80 is encased in enclosure 94 (FIGS. 6A and 6B), open at the bottom 96 to permit entry of liquid. Enclosure 94 also has openings 98 in recessed portion 100. Openings 98 permit viewing of zones 84 to determine the results of an assay utilizing this particular embodiment of the invention. Enclosure 94 also has opening 102, which allows access to distortable portion 92 of second strip of bibulous material 90 so that distortable portion 92 can be bent to contact portion 104 of first strip of bibulous material 82. Enclosure 94 also has openings 93 and 95 for viewing first strip of bibulous material 82.

Figures 7, 8, 9:
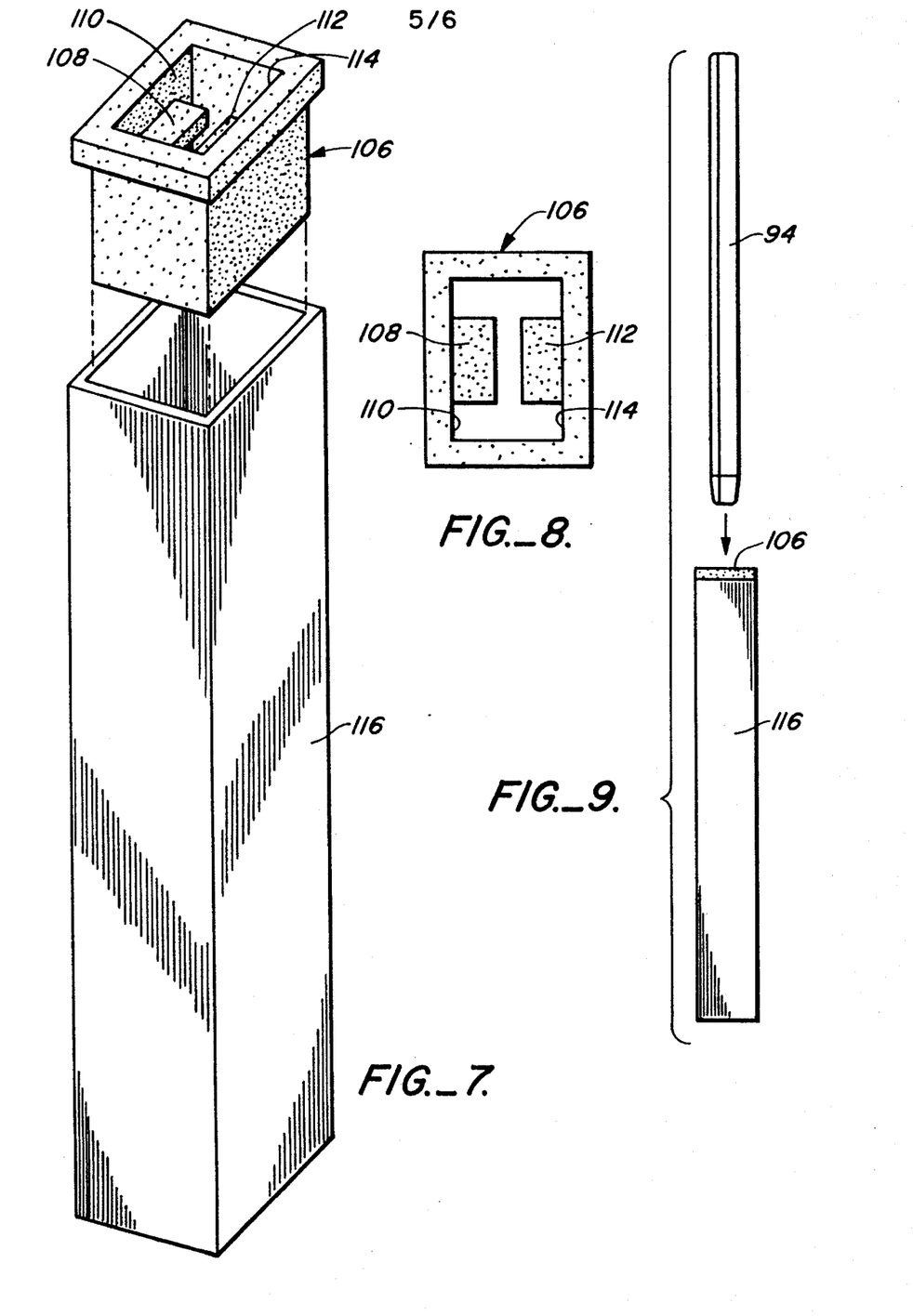
FIG. 7 is an exploded perspective view of a housing and a container for the device of FIGS. 6A and 6B.
FIG. 8 is a top plan view of the housing shown in FIG. 7.
FIG. 9 is a side elevational view depicting the insertion of the device of FIGS. 6A and 6B into the housing and container of FIGS. 7 and 8.
Figure 9A:
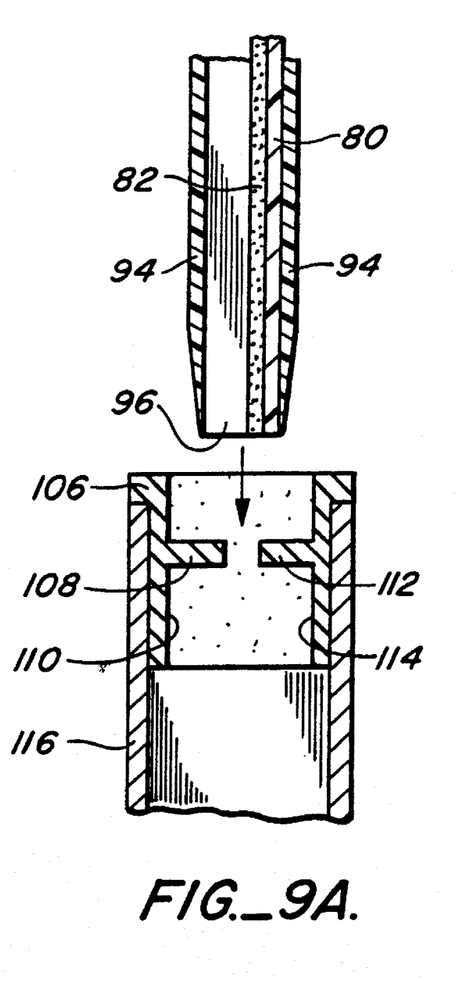
FIGS. 9A–9C are enlarged cross-sectional views showing the progression of the insertion of the device of FIGS. 6A and 6B into the housing and container of FIGS. 7 and 8.
Figure 9B:
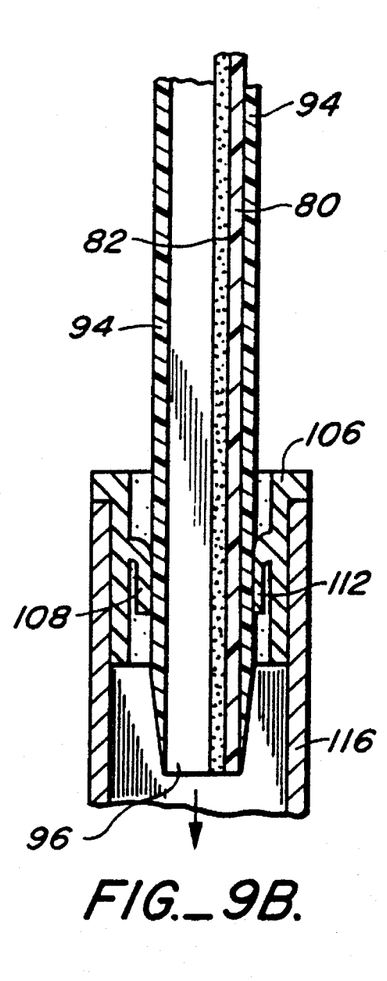
Figure 9C:
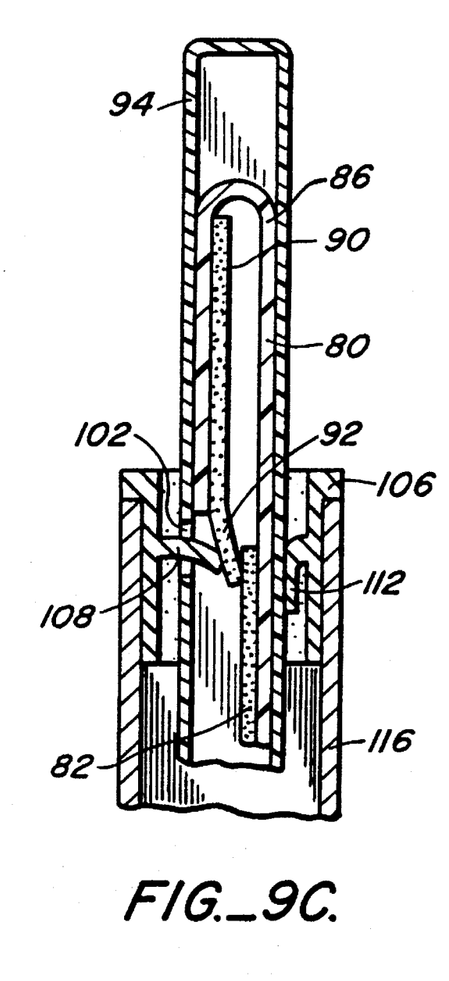

FIG. 7 depicts housing 106 having flexible member 108 fixedly attached to inner wall 110 of housing 106. Flexible member 112 (FIG. 8) is fixedly attached to inner wall 114 of housing 106 opposite flexible member 108. The function of flexible members 108 and 112 will be explained hereinbelow. Housing 106 is adapted to attach to the top of container 116.

Figure 6A:
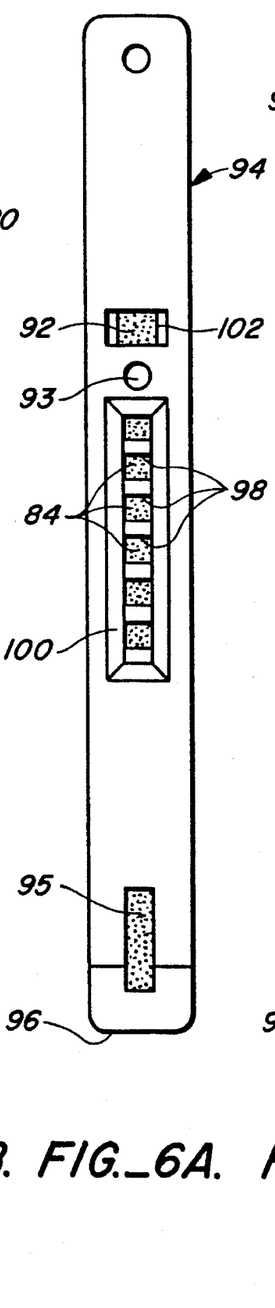
FIG. 6A is a front view of an enclosure for the device of FIGS. 5A and 5B.
Figure 6B:
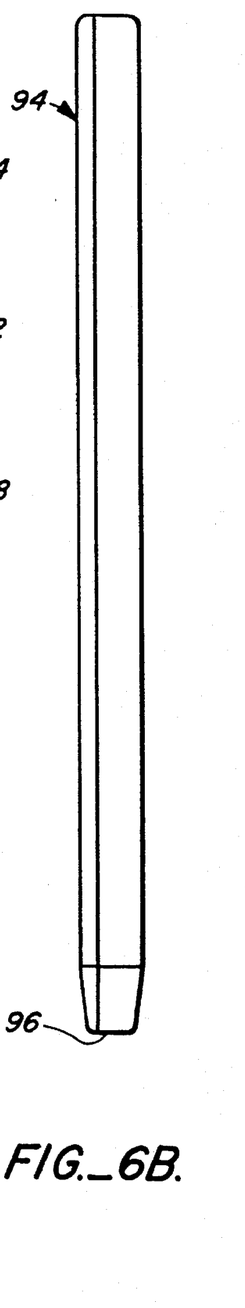
FIG. 6B is a side view of the enclosure of FIG. 6A.

Referring now to FIGS. 9 and 9A–9C, enclosure 94 depicted in FIG. 6A is designed to be inserted into housing 106, which has been fitted into container 116. As enclosure 94 is inserted into housing 106, the portion of enclosure 94 at opening 96 contacts flexible member 108 and flexible member 112. The rigidity of enclosure 94 causes members 108 and 112 to be bent downward (FIG. 9B) thus allowing insertion of enclosure 94. As enclosure 94 moves further into container 116, opening 102 in enclosure 94 is engaged by flexible member 108, which flexes inwardly to contact distortable portion 92 of second strip of bibulous material 90 (FIG. 5A). Flexible member 108 forces distortable portion 92 to contact portion 104 of first strip of bibulous material 82. As a result a capillary flow relationship in initiated between first and second pieces of bibulous material, 82 and 90, respectively. A liquid medium (not shown) in the bottom of container 116 contacts first strip of bibulous material 82, along which it traverses by capillarity into and along second strip of bibulous material 90.

In view of the above, it is apparent that devices of the present invention allow the creation of a longitudinal capillary flow relationship among two or three pieces of bibulous material which theretofore were in a non-capillary flow relationship. Such devices have the particular advantage of allowing the device operator to choose the time to actuate the device and thus create the capillary flow relationship.

The housing used in some of the devices of the present invention as well as the bases and protrusions can be prepared from non-corrodable materials which do not readily degrade or disintegrate upon exposure to the solutions employed in the assay. Additionally, such materials should not interfere with the assay being conducted. In general, metals, metal alloys, glass and rigid and semi-rigid plastic can be used. Preferably, a rigid or a semi-rigid plastic is employed.

The dimensions of the devices of the present invention can vary depending on the particular use, that is, whether the devices are used in immunoassays, etc. The length as measured in the direction of capillary flow of at least one of the pieces of bibulous material employed in a device of the present invention will generally be at least about 10 times the shortest dimension measured perpendicular to the direction of capillary flow and may be 20 or more times the shortest dimension. Other dimensions may be varied considerably depending upon factors such as whether an absorbent pad is employed, the amount of liquid required to be taken up by the assay, whether a wash solution is required or desired for the assay, etc. Likewise, the extent which the constrictable member must compress depends on factors such as the space between the piece of bibulous material affixed to the constrictable member and the two other pieces of bibulous material. Those skilled in the art will be able to construct devices of the present invention having appropriate dimensions in view of the disclosure herein.

The devices of the present invention can be employed to determine, for example, the result of a chemical test particularly by employing a chromatographic step. The present device can find application in a method for determining qualitatively and/or quantitatively the presence or amount, respectively, of an analyte in a sample suspected of containing the analyte. Examples of such methods are described in U.S. Pat. Nos. 4,366,241; 4,740,488; 4,168,146 and 4,435,504, the disclosures of which are incorporated herein by reference and the terms used below have the meanings set out therein, which meanings have been summarized above.

The above methods may be carried out on, among others, a bibulous strip as a stationary solid phase and involving a moving liquid phase. The stationary solid phase can be contacted with a plurality of reagents in a number of different solutions.

Referring to FIG. 2B, for an assay for analyte a member of specific binding pair (sbp member) can be non-diffusively bound to a bibulous strip to form an "immunosorbing zone" which may be all or a portion of piece of bibulous material 18 or 20. The analyte from the sample traverses piece 18 being carried along with a solvent whose front crosses the zone. The analyte, which may be the homologous or reciprocal sbp member to the sbp member bound to the support, becomes bound to the support through the intermediacy of sbp member complex formation. The signal producing system provides the manner by which part or all of the area in the immunosorbing zone to which the analyte is bound may be distinguished from the area in which it is absent.

The incremental movement of the sample through the immunosorbing zone results from the transport of a solution of the sample in an appropriate solvent through the immunosorbing zone due to capillarity.

The solvent is normally an aqueous medium, which may be up to about 40 weight percent of other polar solvents, particularly oxygenated solvents of from 1 to 6, more usually of from 1 to 4 carbon atoms, including alcohols, ethers and the like. Usually, the co-solvents are present in less than about 20 weight percent.

The pH for the medium is usually in the range of 4–11, more usually 5–10, and preferably in the range of about 6.5–9.5. The pH is chosen to maintain a significant level of binding affinity of the sbp members. Various buffers may be used to achieve the desired pH and maintain the pH during the elution. Illustrative buffers include borate, phosphate, carbonate, tris, barbital and the like. The particular buffer employed is not critical, but in individual assays, one buffer may be preferred over another.

Moderate, and desirably substantially constant, temperatures are normally employed for carrying out the assay. The temperatures for the chromatography and production of a detectable signal are generally in the range of about 10°14 50° C., more usually in the range of about 15°–50° C., and frequently are ambient temperatures, that is, about 15°–25° C.

The concentration of analyte which may be assayed generally varies from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions are generally determined by the concentration range of interest of the analyte, the final concentration of each of the reagents is normally determined empirically to optimize the sensitivity of the assay over the range of interest. However, with certain protocols, individual reagents may be used in substantial excess without detrimentally affecting the sensitivity of the assay.

Other reagents which are members of the signal producing system can vary widely in concentration depending upon the particular protocol and their role in signal production.

In carrying out the assay, the protocol normally involves dissolving the sample into the eluting solvent. The sample may be derived from a wide variety of sources, such as physiologic fluids, illustrated by blood, serum, plasma, urine, ocular lens fluid, spinal fluid, etc., chemical processing streams, food, pesticides, pollutants, etc.

The bottom or proximal end of device 10 (i.e., the end of device 10 (FIG. 1) that is contacted with the liquid medium) is contacted with the sample dispersed in the solvent, which is normally a buffered aqueous medium which may contain one or more members of the signal producing system. Where a member of the signal producing system is present, at least one member is usually conjugated to a sbp member to provide a sbp member-label conjugate.

Sufficient time is allowed for the solvent front to complete traversal of piece of bibulous material 18.

For the most part, relatively short times are involved. Usually, the traverse of the sample through first piece 18 takes at least 30 sec and not more than 1 hour, more usually from about 1 min to 30 min.

A solutions that may include other reagents including signal producing system members not included with the sample solution or on piece 18 or 20 are then contacted with device 10, and pressure is applied to arms 12 and 14 to bring piece of bibulous material 22 into contact with pieces of bibulous material 18 and 20, respectively. This solution then migrates along piece of bibulous material 18 and subsequently along piece of bibulous material 20. After a suitable time the immunosorbing zone is examined for the presence of signal. The development of the signal generally ranges from 30 sec to 30 min, more usually from about 30 sec. to 5 min.

For quantitative assays, a standard sample can be provided having a known amount of analyte. The analyte sample and the standard are each run on a different device 10, and a quantitative comparison is made between the standard sample and the analyte sample. If necessary, more than one standard can be employed, so that the distance traversed for the different concentrations can be used to quantitate a particular sample.

In carrying out an assay (see, for example, U.S. Ser. No. 928,771 filed Nov. 7, 1986, the disclosure of which is incorporated herein by reference) utilizing an apparatus as depicted in FIGS. 5–9, the protocol will normally involve combining in an aqueous medium the sample suspected of containing the analyte with a first sbp member to form the aqueous test solution. The sample may be derived from a wide variety of sources, such as physiologic fluids, illustrated by saliva, blood, serum, plasma, urine, ocular lens fluid, spinal fluid, etc., food products such as milk and wine, chemical processing streams, food waste water, etc.

A contact portion of first strip of bibulous material 82 (FIG. 5B), usually an end portion below the area containing zones 84, is contacted with the test solution, usually by dipping of the contact portion into the test solution. However, contact of the piece of bibulous material with the test solution can be carried out by other techniques such as by spotting the test solution on first piece of bibulous material 82. Wetting of the strip by capillary action usually is allowed to continue, for example, until the liquid front passes the last of zones 84.

For the most part, relatively short times are involved for the test solution to traverse first strip 82. Usually, the traverse of the test solution over strip 82 will take at least 30 sec and not more than 1 hour, more usually from about 1 min to 30 min.

After the liquid has traversed first strip 82 at least past the last of zones 84, enclosure 94 is removed from contact with any test solution that has not been absorbed. A liquid medium that can contain any additional chemical reagents that form part of the signal producing means that includes a label, is then placed in container 116 and housing 106 is fitted into the top of 116. Next, enclosure 94 is inserted into housing 106. The contact portion of the first strip 82 contacts the liquid medium. When flexible member 108 engages opening 102 in enclosure 94, flexible member 108 contacts distortable portion 92 of second strip of bibulous material 90, forcing distortable portion 92 to contact portion 104 of first strip 82. As a consequence a capillary flow relationship is created between strips 82 and 90 respectively.

After contacting the strip with the liquid medium, first strip 82 is contacted with a developer solution containing any remaining members of the signal producing system not present in the sample solution or the subsequent liquid medium, or present on strip 82. When an enzyme is used as a label, a substrate will normally be in substantial excess in the developer solution, so as not to be rate limiting (greater concentration than Km). The developer solution will usually be appropriately buffered for the enzyme system. A sufficient time is allowed to elapse prior to measuring the signal to allow liquid to fully wet first strip 82 and to produce an amount of the signal producing compound required to define the region of the zone in which the analyte or analytes are bound. Once the detectable signal has been produced, the presence or absence of the analyte or analytes in the sample is known.

The strips can be coated with a wide variety of materials to provide for enhanced properties. Coatings may include protein coatings, polysaccharide coatings, synthetic polymers, sugars or the like, which are used particularly to enhance the stability of the materials conjugated to the strip. These compounds can also be used for improved binding of the materials, such as antibody binding or the like.

The strip, or the zones, can be activated with reactive functionalities to provide for covalent bonding of the organic materials to be conjugated to the strip such as those described in U.S. Pat. No. 4,168,146, the relevant disclosure of which is incorporated herein by reference.

As mentioned above one embodiment of this invention can be employed to assay a sample suspected of containing one or more of a plurality of analytes such as drugs, thus screening for the presence of one or more of such analytes. In this situation the test solution is formed by mixing together in an appropriate liquid medium the sample and a plurality of first sbp members, e.g., conjugates each comprising one of the analytes and a label. If it is only desired to know if any one of the drugs is present such as in a screening assay, first strip 82 contains a single zone, such as would be employed for a single drug, to which is bound a binding agent capable of specifically binding each of the first sbp members. If it is necessary to know which drugs are present, strip 82 contains a separate, preferably non-contiguous, zone for each drug (as depicted in FIG. 5B). To each zone is bound a binding agent such as a second sbp member capable of specifically binding to a different first sbp member. In either case it is necessary to have non-diffusively and preferably homogeneously bound on the strip between the zones and the contact portion a plurality of second sbp members each respectively capable of binding one of the above first sbp members.

As a result of the present invention the above assay protocols are greatly simplified by eliminating or reducing the need for precise timing and accurate volumetric dispensing.

Sbp members can be diffusively or non-diffusively bound to one or more pieces of bibulous material utilized in the present invention.

To enhance the versatility of the subject invention, the device or apparatus can be provided in packaged combination with a liquid medium and other components in the same or separate containers as the interreactivity of the components permit. For conducting an assay the kit can further include other separately packaged reagents for conducting an assay including members of the signal producing system, antibodies either labeled or unlabeled, supports, ancillary reagents, and so forth. Reagents can be provided so that the ratio of the reagents provides for substantial optimization of the method and assay.

Having described several embodiments of devices and methods of the present invention, by way of example and not limitation, it is to be understood that various changes in form and detail may be made therein without departing from the scope and spirit of this invention or the scope of the appended claims.

What is claimed is:

1. A kit for conducting an assay comprising in packaged combination:

(a) a support having two pieces of bibulous material fixedly attached thereto in a non-capillary flow relationship to each other, (b) a housing having a flexible member fixedly attached thereto, wherein said support is adapted for insertion into said housing and said flexible member is adapted to force one of said two pieces of bibulous material into contact with the other of said two pieces of bibulous material upon insertion of said support into said housing thereby forming a device which permits longitudinal capillary flow of a liquid through said two pieces of bibulous material and (c) separately packaged reagents for conducting an assay said reagents comprising at least one member of a signal producing signal.

2. The kit according to claim 1 wherein at least one of said two pieces of bibulous material has a member of a specific binding pair bound thereto.

3. The kit according to claim 1 comprising a container adapted to attach to said housing.

4. An apparatus which provides for longitudinal capillary flow of a liquid through two pieces of bibulous material which prior to actuation are in a non-capillary flow relationship to each other, which apparatus comprises:

(a) a support having two pieces of bibulous material fixedly attached thereto in a non-capillary flow relationship to each other and (b) a housing having a flexible member fixedly attached thereto, said support being adapted for insertion into said housing and said flexible member being adapted to force one of said two pieces of bibulous material into contact with the other of said two pieces of bibulous material upon insertion of said support into said housing thereby forming a device which permits longitudinal capillary flow of a liquid through said two pieces of bibulous material.

5. The apparatus according to claim 4 comprising a container wherein said housing and said container are adapted to be attached together.

6. An apparatus according to claim 4 wherein said support is contained in an enclosure.

7. An apparatus according to claim 4 comprising a second flexible member fixedly attached to said housing opposite said flexible member.

8. An apparatus according to claim 4 wherein said pieces of bibulous material are paper strips.

9. An apparatus according to claim 4 wherein one of said pieces of bibulous material has a member of a specific binding pair bound thereto.

* * * * *